(12) United States Patent
Nishina et al.

(10) Patent No.: US 7,587,288 B2
(45) Date of Patent: Sep. 8, 2009

(54) CONDITION DISCRIMINATING APPARATUS FOR LIQUID REDUCING AGENT

(75) Inventors: Mitsuhiro Nishina, Ageo (JP); Toshikazu Katou, Ageo (JP); Eitarou Asakawa, Ageo (JP)

(73) Assignee: Nissan Diesel Motor Co., Ltd., Saitama (JP)

( * ) Notice: Subject to any disclaimer, the term of this patent is extended or adjusted under 35 U.S.C. 154(b) by 238 days.

(21) Appl. No.: 11/790,759

(22) Filed: Apr. 27, 2007

(65) Prior Publication Data

US 2007/0204678 A1 Sep. 6, 2007

Related U.S. Application Data

(63) Continuation of application No. PCT/JP2005/017284, filed on Sep. 20, 2005.

(30) Foreign Application Priority Data

Oct. 29, 2004 (JP) ............................. 2004-315615

(51) Int. Cl.
*G06F 19/00* (2006.01)
(52) U.S. Cl. ...................................... 702/50
(58) Field of Classification Search ............... 73/53.01, 73/61.46, 61.76; 702/25, 50, 55, 100, 130
See application file for complete search history.

(56) References Cited

U.S. PATENT DOCUMENTS

| | | | | |
|---|---|---|---|---|
| 6,063,350 | A * | 5/2000 | Tarabulski et al. | 423/239.1 |
| 6,119,448 | A * | 9/2000 | Emmerling et al. | 60/274 |
| 6,343,467 | B1 * | 2/2002 | Muto et al. | 60/285 |
| 6,519,935 | B2 * | 2/2003 | Weigl | 60/286 |
| 7,017,335 | B2 * | 3/2006 | Huber et al. | 60/286 |
| 7,065,958 | B2 * | 6/2006 | Funk et al. | 60/286 |
| 7,467,512 | B2 * | 12/2008 | Nishina et al. | 60/286 |
| 2004/0045284 | A1 * | 3/2004 | Ripper et al. | 60/286 |
| 2005/0011183 | A1 | 1/2005 | Ripper et al. | |
| 2007/0075467 | A1 | 4/2007 | Osaku et al. | |
| 2007/0079599 | A1 * | 4/2007 | Osaku et al. | 60/283 |
| 2007/0204677 | A1 * | 9/2007 | Nishina et al. | 73/53.01 |

(Continued)

FOREIGN PATENT DOCUMENTS

JP 04-282433 10/1992

(Continued)

*Primary Examiner*—John Fitzgerald
(74) *Attorney, Agent, or Firm*—McDermott Will & Emery LLP (57) ABSTRACT

Each of a first and a second number of times is counted, in which the first number of times indicates a condition where a concentration of a liquid reducing agent indirectly measured based on a characteristic of heat transmission between two separated points is successively determined to be equal to or higher than an upper limit threshold for no agent, and the second number of times indicates a condition the concentration is successively determined to be equal to or lower than a lower limit threshold for different agent. When the former becomes equal to or larger than the predetermined value, determination is made that no liquid reducing agent remains. When, the latter becomes equal to or larger than the predetermined value, determination is made that the liquid reducing agent is a solution of a different kind. When the former and the latter is less than the predetermined value, determination is made that correct liquid reducing agent remains.

6 Claims, 10 Drawing Sheets

U.S. PATENT DOCUMENTS

2007/0209428 A1* 9/2007 Nishina et al. ............. 73/61.76

FOREIGN PATENT DOCUMENTS

| | | |
|---|---|---|
| JP | 2000-027627 | 1/2000 |
| JP | 2001-020724 | 1/2001 |
| JP | 2002-508466 | 3/2002 |
| JP | 2002-513109 | 5/2002 |
| JP | 2002-527660 | 8/2002 |
| JP | 2002-370016 | 12/2002 |
| JP | 2002-371831 | 12/2002 |
| JP | 2004-517336 | 6/2004 |
| JP | 2004-257325 | 9/2004 |
| JP | 2005-308888 | 2/2005 |
| WO | WO 99/30810 | 6/1999 |
| WO | WO 99/55445 | 11/1999 |
| WO | WO 00/21881 | 4/2000 |
| WO | WO 02/27280 | 4/2002 |
| WO | WO 02/057603 | 7/2002 |
| WO | WO 2005/005971 | 1/2005 |

* cited by examiner

CONDITION DISCRIMINATING APPARATUS FOR LIQUID REDUCING AGENT

This application is a continuation of PCT/JP2005/17284, filed on Sep. 20, 2005.

BACKGROUND OF THE INVENTION

1. Field of the Invention

The present invention generally relates to a catalytic purifying system for reducing nitrogen oxide (NOx) contained in an exhaust emission, and in particular to a technique enabling it for a computer-incorporated control unit to always discriminate that there is no remainder of a liquid reducing agent, there remains a different kind of liquid agent, or there is a liquid reducing agent that is normal by using a sensor unit capable of issuing an output signal in relation to the concentration of a liquid reducing agent on the basis of a characteristic of heat transmission between two points apart from each other within a storage tank capable of storing the liquid reducing agent.

2. Description of the Related Art

As a catalytic purification system for reducing nitrogen oxide ($NO_X$) included in engine exhaust gas, Japanese Unexamined Patent Publication No. 2000-27627 discloses an exhaust gas purifying apparatus. In the exhaust gas purifying apparatus, a liquid reducing agent of a necessary amount depending on the engine operating conditions is injected into an exhaust gas moving on an upstream side of a reduction catalytic converter, which is disposed in an engine exhaust system to make a catalytic reduction reaction between $NO_X$ in the exhaust gas and the liquid reducing agent, thereby converting $NO_X$ to harmless components.

In the conventional exhaust gas purifying apparatus, however, when purification efficiency changes as the concentration of the liquid reducing agent changes, if the driver continues the operation of an engine without noticing it, required $NO_X$ reducing performance cannot be achieved, and there occurs such an undesirable potential that a large amount of $NO_X$ is inconveniently exhaust into the atmosphere. In particular, when there is no remainder of the liquid reducing agent or there remains a solution of a different kind which does not function as a liquid reducing agent is used, the above-mentioned inconvenient problem conspicuously appears.

Consequently, it has been contrived to provide such a sensor that is able to detect concentration of a liquid reducing agent on the basis of the characteristic of heat transmission between two points within the liquid reducing agent which are separated apart from each other. However, when the sensor is mounted on a mobile vehicle such as a car, the following problem might occur. Specifically, since the vehicle body is constantly subjected to vibrations due to the waviness of the road surfaces and the like while a mobile vehicle is running, convective motion of the liquid reducing agent is generated in a storage tank. When the convection is generated in the liquid reducing agent, the heat transmission characteristic of the liquid reducing agent workable as a heat transmission medium changes, and the concentration detection accuracy accordingly deteriorates quite a lot. Consequently, it becomes difficult to detect concentration of the liquid reducing agent during travel of the mobile vehicle, and it cannot be said that the sensor is sufficiently utilized.

SUMMARY OF THE INVENTION

In view of the problems of the conventional technique as described above, an object of the present invention is to provide a liquid reducing agent discriminating apparatus capable of always discriminating one from such three conditions that there is no remainder of liquid reducing agent, there remains a different kind of liquid or solution, and there is a liquid reducing agent that is normal by using the fact that, as long as the liquid reducing agent is normal one, even when convection occurs, it is extremely rare that a sensor output deviates from a predetermined range a number of times in a row.

Therefore, the present invention provides a liquid reducing agent discriminating apparatus comprising: a sensor disposed in a storage tank capable of storing a liquid reducing agent and configured to output a signal in relation to concentration of the liquid reducing agent on the basis of a characteristic of heat transmission between two points apart from each other within the storage tank; and a control unit having therein a computer, wherein the control unit outputs a measurement trigger at an every predetermined time after start of an engine, calculates concentration of the liquid reducing agent on the basis of the signal from the sensor upon outputting of the measurement trigger, counts each of first number of times when the concentration successively becomes equal to or higher than a predetermined upper limit threshold and second number of times when the concentration successively becomes equal to or lower than a predetermined lower limit threshold, determines that there is no remainder of liquid reducing agent when the first number of times becomes equal to or larger than a predetermined value, and, determines that there remains a solution of a different kind from the liquid reducing agent when the second number of times becomes equal to or larger than the predetermined value.

The liquid reducing agent discriminating apparatus of the invention uses such a true fact that, as long as the liquid reducing agent is normal solution, even when convection occurs, it is extremely rare that a sensor output deviates from a predetermined range a number of times in a row. When the number of times that the concentration of the liquid reducing agent is determined to be equal to or higher than a predetermined upper limit threshold or is equal to or lower than a predetermined lower limit threshold in a row becomes a predetermined value or larger, the liquid reducing agent discriminating apparatus determines that there is no remainder of liquid reducing agent or there remains a solution different kind from the liquid reducing agent. Consequently, irrespective of the state that a vehicle is left to be in, it can be always discriminated that there is no remainder of liquid reducing agent or there remains a solution different in its kind from the liquid reducing agent.

DESCRIPTION OF THE PREFERRED EMBODIMENTS

The present invention will be described in detail hereinbelow with reference to the accompanying drawings.

Figure 1:
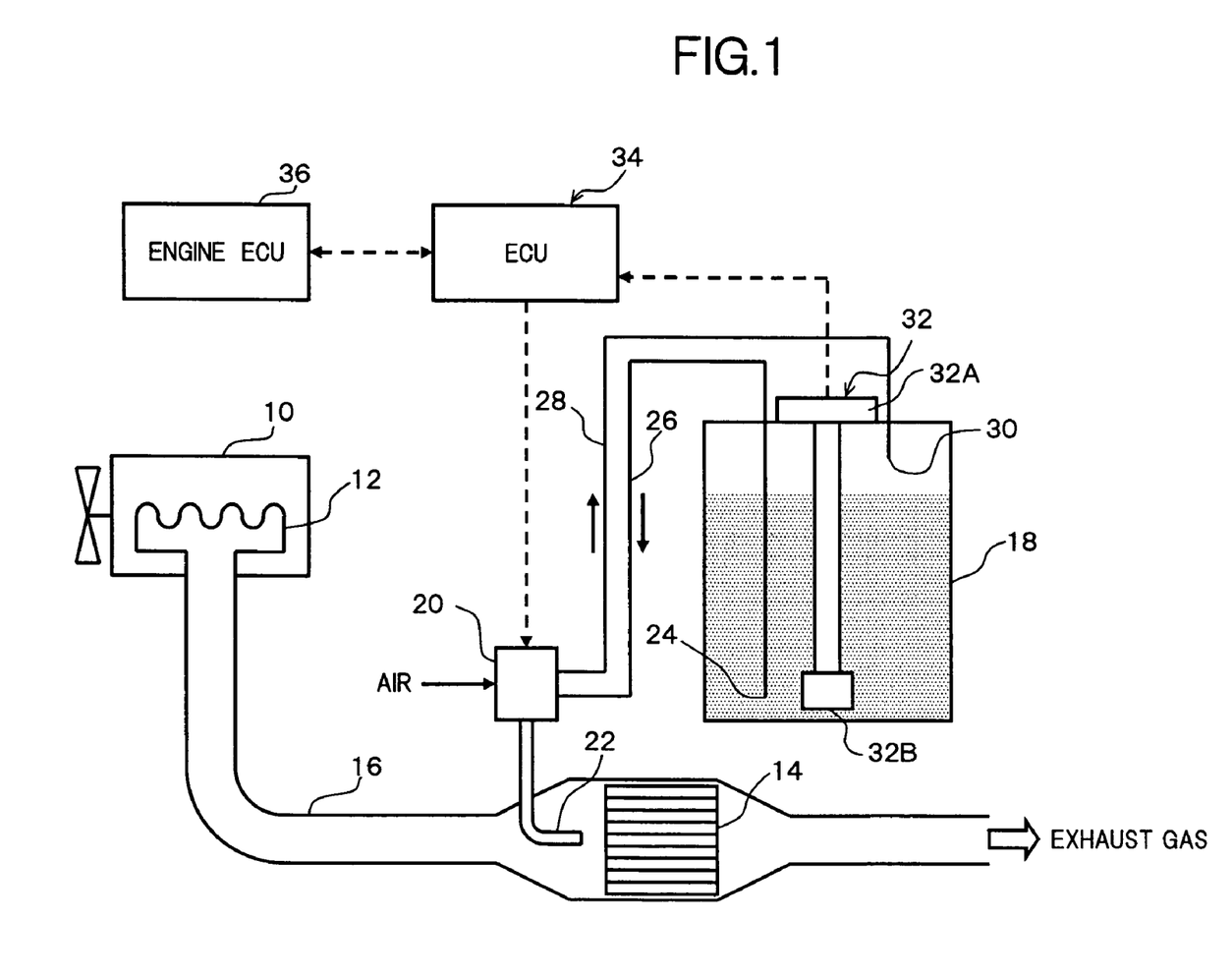
FIG. 1 is a diagrammatic view showing a general configuration of an exhaust gas purifying system for a vehicle engine, provided with a liquid reducing agent discriminating apparatus according to the present invention.

Referring to FIG. 1, which shows a general configuration of an exhaust gas purifying system provided with a liquid reducing agent discriminating apparatus according to the present invention, an exhaust gas of an engine 10 is exhausted from an exhaust manifold 12 to atmosphere through an exhaust pipe 16 in which an $NO_X$ reduction catalytic converter 14 is disposed. Specifically, in the exhaust pipe 16, in order from the exhaust upstream side, three catalytic converters of an oxidation catalytic converter of nitric oxide (NO), an $NO_X$ reduction catalytic converter, and a slip ammonia oxidation catalytic converter are disposed. A temperature sensor, an oxygen sensor, and the like are disposed before and after the three catalytic converters, thereby constructing an exhaust system (the details are not shown). On the exhaust upstream of the $NO_X$ reduction catalytic converter 14, a liquid reducing agent stored in a storage tank 18 is injected together with air through a reducing agent supplying device 20 and an injection nozzle 22. Although a urea aqueous solution is used as the liquid reducing agent in the embodiment, an ammonia aqueous solution, or diesel oil, petroleum, gasoline, in which hydrocarbon is included as a main component, or the like may be used.

The urea aqueous solution is a solution in which solid or powder urea is dissolved. The urea aqueous solution is sucked from a suction port 24 opened in a lower position near the bottom of the storage tank 18 and is supplied to the reducing agent supplying device 20 through a supply pipe 26. An excess, which does not contribute to injection, of the urea aqueous solution supplied to the reducing agent supplying device 20 passes through a return pipe 28 and is returned to the storage tank 18 from a return port 30 opened in an upper position in the storage tank 18.

The urea aqueous solution injected on the exhaust upstream of the $NO_X$ reduction catalytic converter 14 is hydrolyzed with exhaust heat and steam in the exhaust gas, so that ammonia is easily generated. It is known that the generated ammonia reacts with $NO_X$ in the exhaust in the $NO_X$ reduction catalytic converter 14 and is converted to water and harmless gas.

To the storage tank 18, a sensor 32 that is configured to output a signal related to the concentration of the urea aqueous solution is attached. Specifically, a base unit 32A having therein a circuit board is secured to the ceiling of the storage tank 18, and a detecting unit 32B is hung down from the base unit 32A toward the bottom of the storage tank 18.

Figure 2:
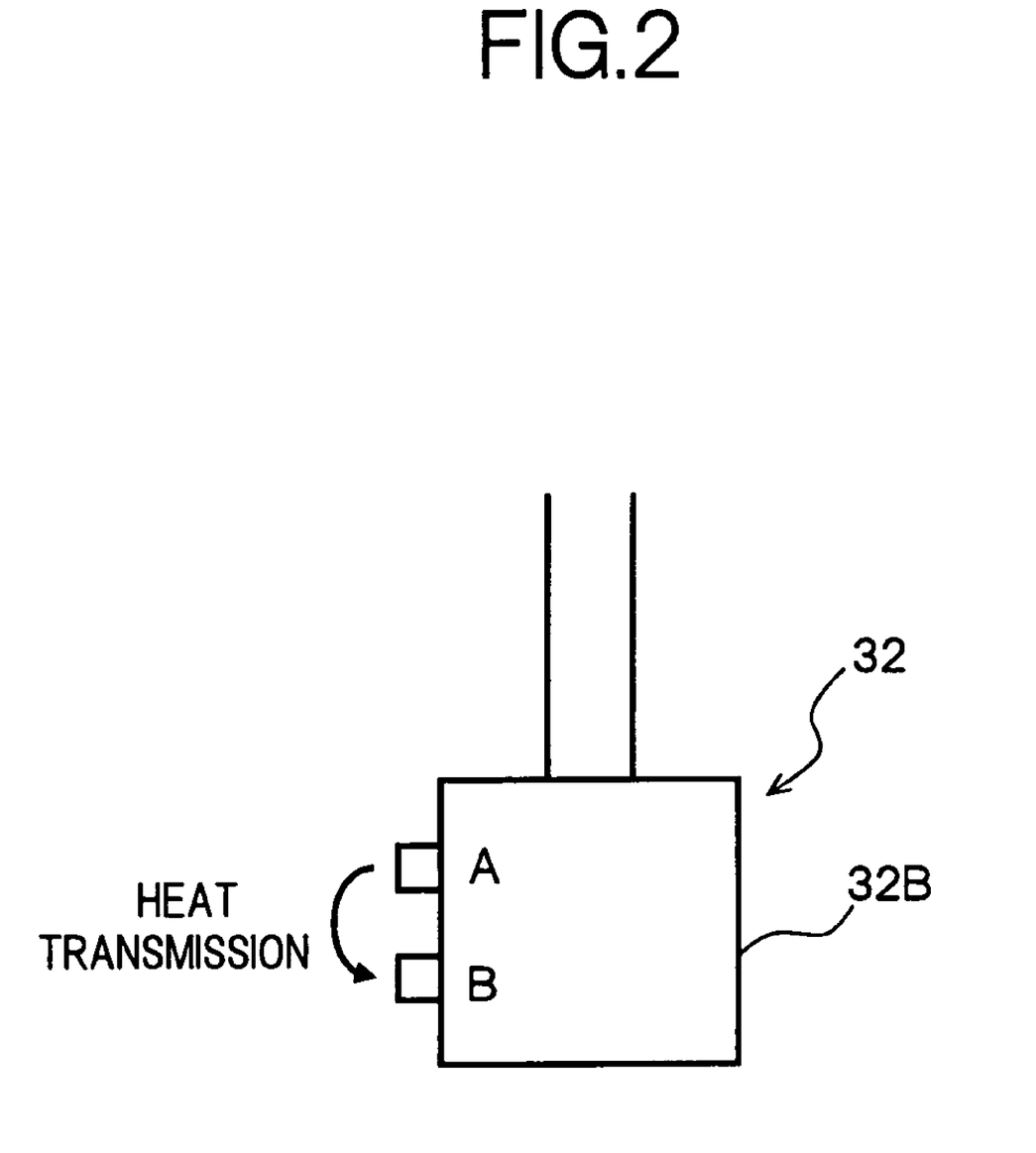
FIG. 2 is a detailed diagrammatic view of a detecting unit of a sensor.
Figure 3:
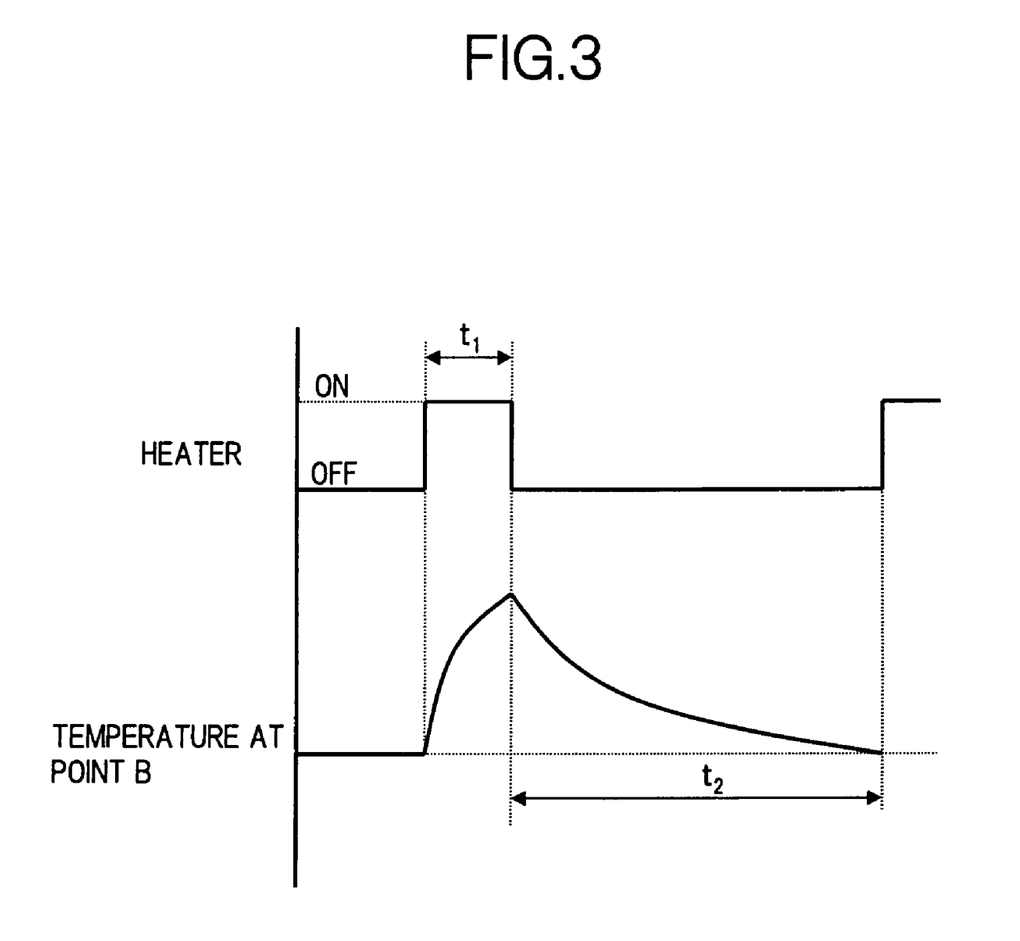
FIG. 3 is a diagrammatic view showing the principle of detecting a liquid concentration by the sensor.

As the detecting unit 32B, as shown in FIG. 2, a heater A and a temperature sensor B are disposed in two positions apart from each other, which are located within the storage tank. When the heater A operates, a signal related to concentration of the urea aqueous solution is outputted on the basis of the characteristic of heat transmitted to the temperature sensor B. To be concrete, as shown in FIG. 3, when the heater A is operated for a predetermined time $t_1$, the temperature in the temperature sensor B gradually increases with the characteristic according to thermal conductivity of the urea aqueous solution. The concentration of the urea aqueous solution can be indirectly detected according to the temperature rise characteristic when the heater A is stopped, that is, the difference between the initial temperature and the peak temperature in the temperature sensor B. On the other hand, after the heater A is stopped, the temperature in the temperature sensor B gradually drops to the temperature before the heater operates by taking time $t_2$. Consequently, the concentration of the urea aqueous solution can be detected every predetermined time $(t_1+t_2)$. As the sensor 32, a sensor manufactured and sold by Mitsui Mining & Smelting Co., Ltd. is known.

Figure 4:
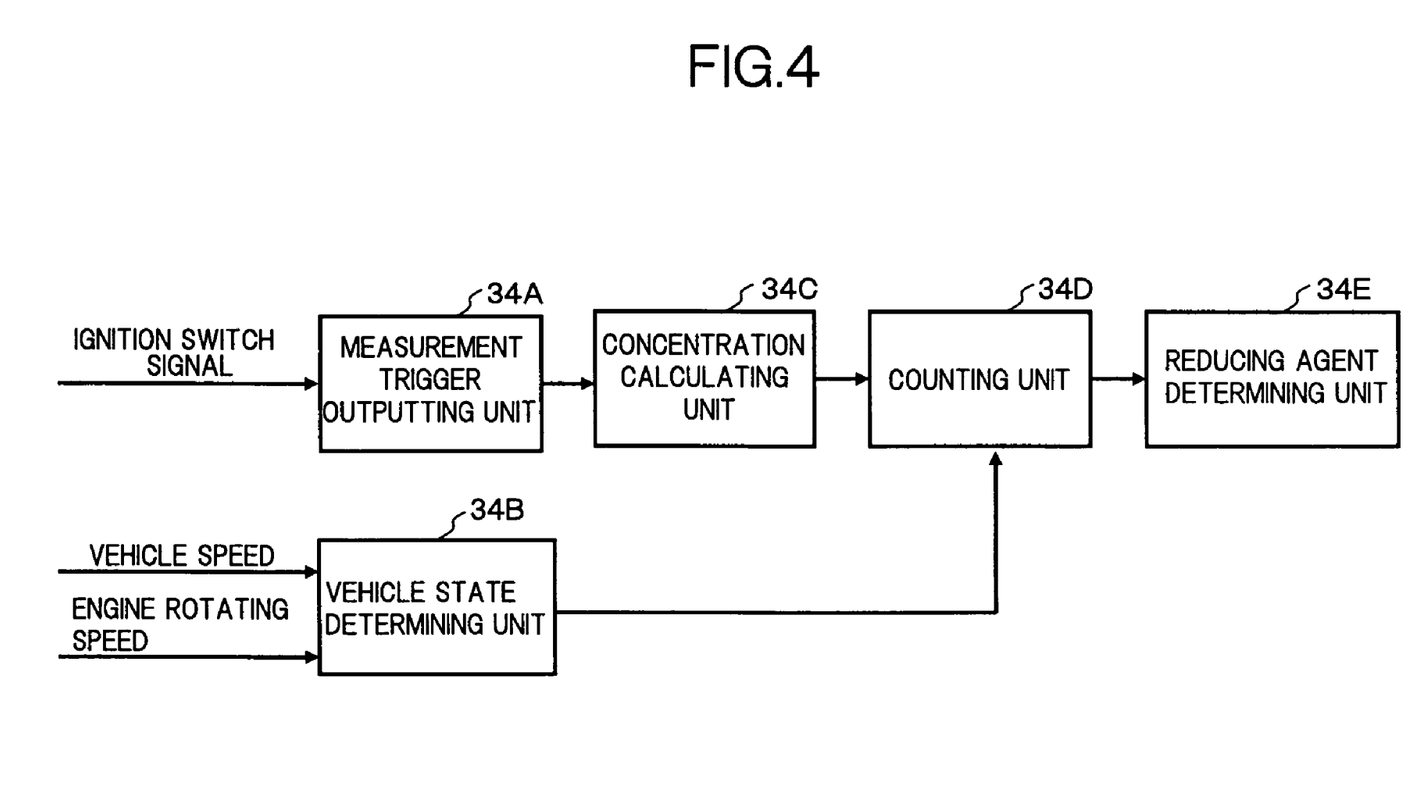
FIG. 4 is a block diagram showing various functions constituting a liquid reducing agent discriminating apparatus.

An output signal of the sensor 32 is inputted to a control unit 34 having therein a computer. To the control unit 34, an engine rotating speed signal, an ignition switch signal, a vehicle speed signal, and the like are inputted from an engine control unit 36 for performing various controls on the engine 10 via a CAN (Controller Area Network) or the like. In the control unit 34, by a control program stored in a ROM (Read Only Memory), as shown in FIG. 4, a measurement trigger outputting unit 34A, a vehicle state determining unit 34B, a concentration calculating unit 34C, a counting unit 34D, and a reducing agent determining unit 34E are realized. In the embodiment, the engine control unit 34 has the functions of an engine rotating speed detector and a vehicle speed detector. Alternatively, the engine rotating speed and the vehicle speed may be separately detected by known sensors.

The measurement trigger outputting unit 34A is activated when the ignition switch signal is made on, and outputs a measurement trigger indicating that detection of concentration of the urea aqueous solution is to be started at an every predetermined time $(t_1+t_2)$ shown in FIG. 3. The vehicle state determining unit 34B determines whether the vehicle is stopped or running on the basis of the vehicle speed signal and the engine rotating speed signal. The concentration calculating unit 34C calculates the concentration of the urea aqueous solution on the basis of the signal from the sensor 32 when the measurement trigger is outputted from the measurement trigger outputting unit 34A. The counting unit 34D counts the number of times the concentration of the urea aqueous solution calculated by the concentration calculating unit 34C continuously deviates from a predetermined range in accordance with the vehicle state determined by the vehicle state determining unit 34B. The reducing agent determining unit 34E determines that the liquid reducing agent is not a correct reducing agent when the number of counting times by the counting unit 34D becomes equal to or larger than a predetermined value.

Next, the action of the liquid reducing agent discriminating apparatus will be described with reference to the flowcharts of FIGS. 5 through 9.

Figure 5:
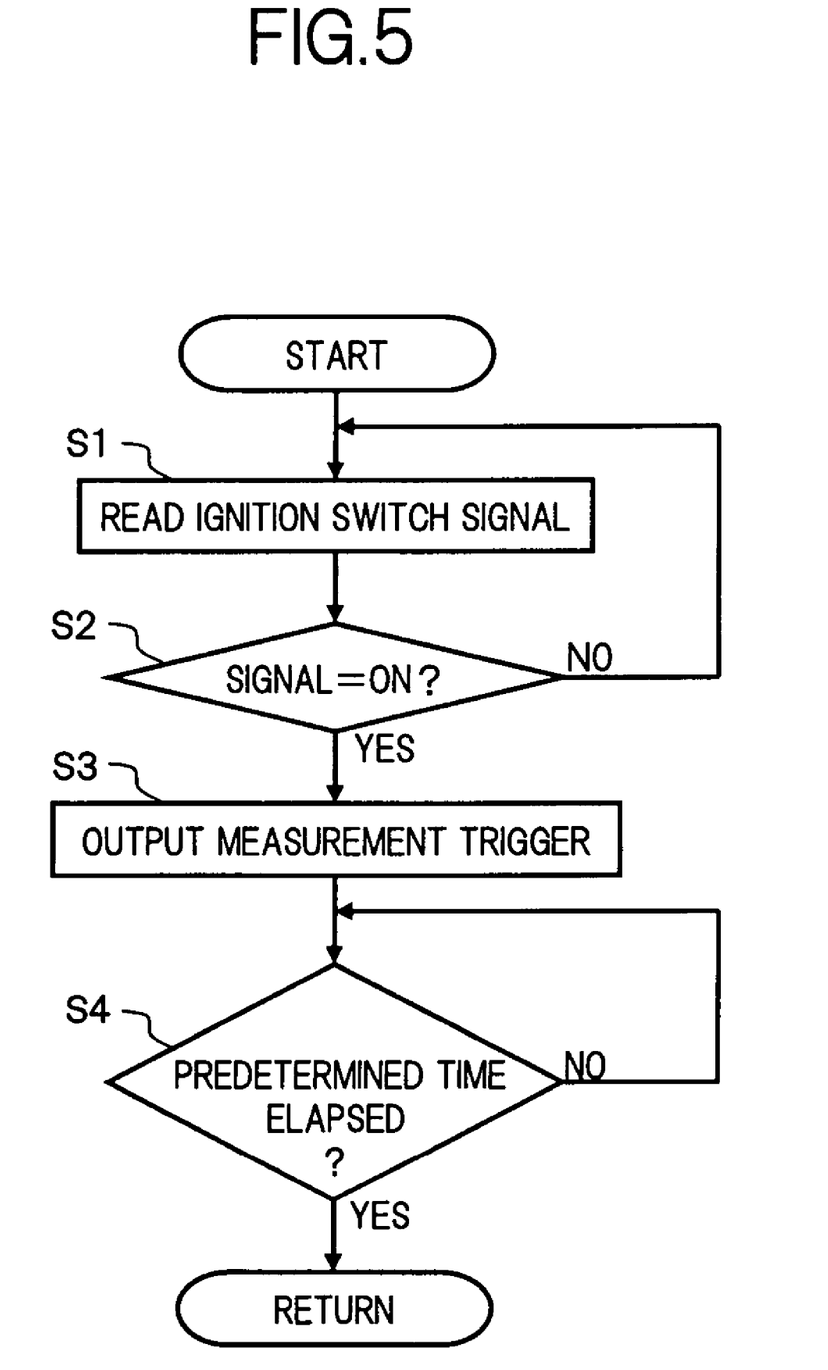
FIG. 5 is a flowchart showing a measurement trigger output process.

In FIG. 5 showing the measurement trigger outputting process performed by the measurement trigger outputting unit 34A, in step 1 (S1 in the diagram, and other steps are similarly written below), an ignition switch signal is read from the engine control unit 36 via a CAN or the like.

In step 2, whether the ignition switch signal is ON or not, in other words, whether the engine 10 has started or not is determined. When the ignition switch signal is ON (Yes), the program proceeds to step 3. When the ignition switch signal is OFF (No), the program returns to step 1.

In step 3, the measurement trigger is outputted.

In step 4, whether predetermined time $(t_1+t_2)$ has elapsed since the measurement trigger was outputted or not is determined. When the predetermined time has elapsed since the measurement trigger was outputted (Yes), the process is terminated. When the predetermined time has not elapsed (No), the apparatus waits.

In the measurement trigger outputting process, after the engine 10 starts, the measurement trigger is outputted every predetermined time $(t_1+t_2)$. Consequently, by monitoring the presence or absence of the measurement trigger, whether detection of the concentration of the urea aqueous solution by the sensor 32 is enabled or not can be grasped.

Figure 6:
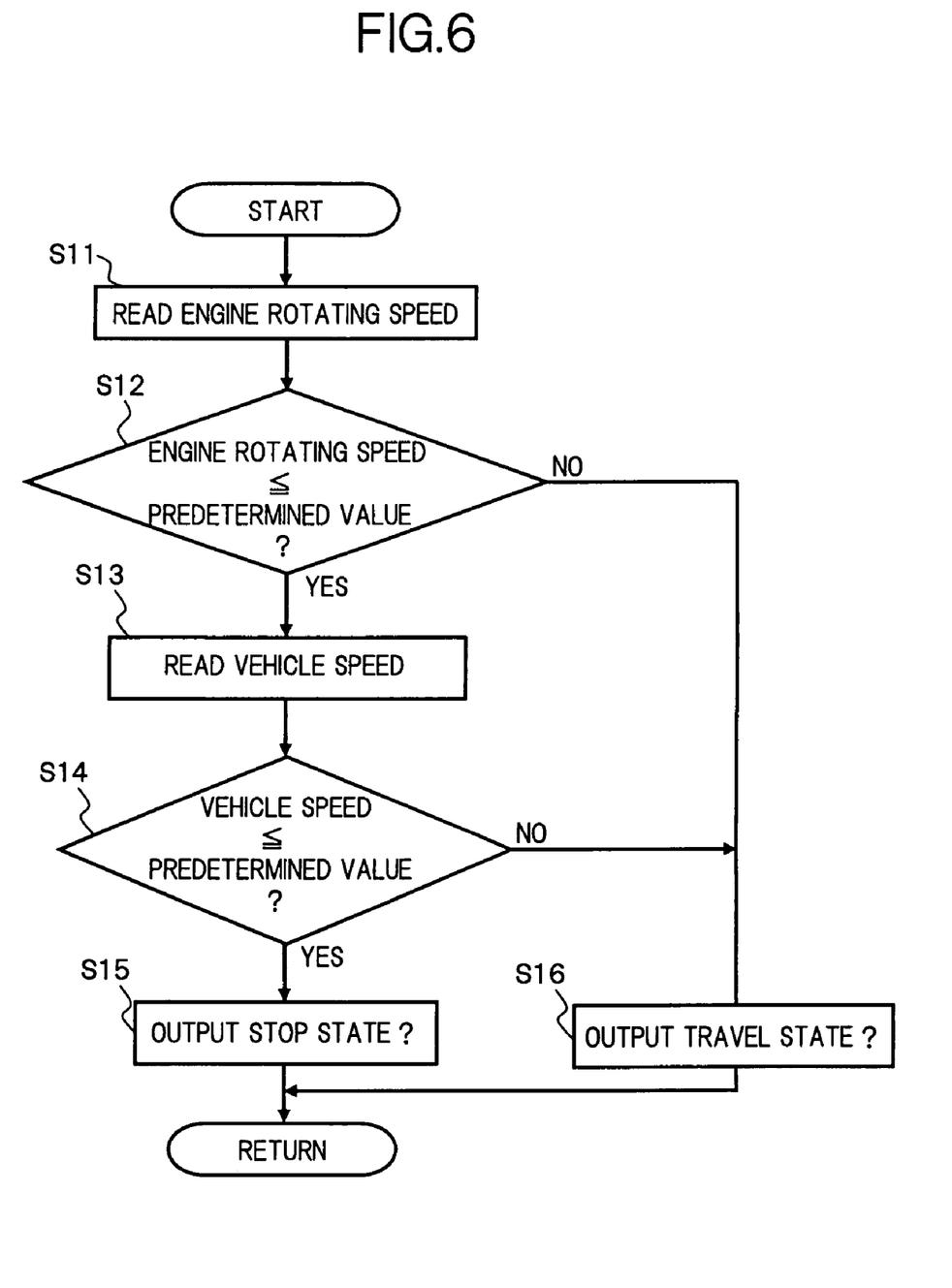
FIG. 6 is a flowchart showing a vehicle state determining process.

In FIG. 6 showing a vehicle state determining process performed by the vehicle state determining unit 34B, in step 11, the engine rotating speed signal is read from the engine control unit 36 via a CAN or the like.

In step 12, whether the engine rotating speed is equal to or less than a predetermined value or not, in other words, whether the engine 10 is idling or not is determined. When the engine rotating speed is equal to or less than the predetermined value (Yes), the program proceeds to step 13. When the engine rotating speed is higher than the predetermined value (No), the program proceeds to step 16.

In step 13, the vehicle speed signal is read from the engine control unit 36 via a CAN or the like.

In step 14, whether the vehicle speed is equal to or less than a predetermined value or not, in other words, whether the speed of the vehicle is equal to or less than a value of the vehicle stop state or not is determined. When the vehicle speed is equal to or less than the predetermined value (Yes), the program proceeds to step 15. When the vehicle speed is higher than the predetermined value (No), the program proceeds to step 16.

In step 15, it is determined that the vehicle stops, and data indicative of the stop state is outputted. The data indicative of the stop state is outputted to a predetermined area in a memory so that it can be referred to in any time.

In step 16, it is determined that the vehicle is running and data indicative of the travel state is outputted. Like the data indicative of the stop state, the data indicative of the travel state is outputted to a predetermined area in a memory so that it can be referred to in any time.

In the vehicle state determining process, when the engine rotating speed is equal to or less than the predetermined value and the vehicle speed is equal to or less than the predetermined value, the "stop state" is determined. In the other cases, the "travel state" is determined. When the vehicle stops, considering the fact that the engine 10 is idling and the vehicle speed is almost zero, the vehicle state can be determined with high accuracy.

Figure 7:
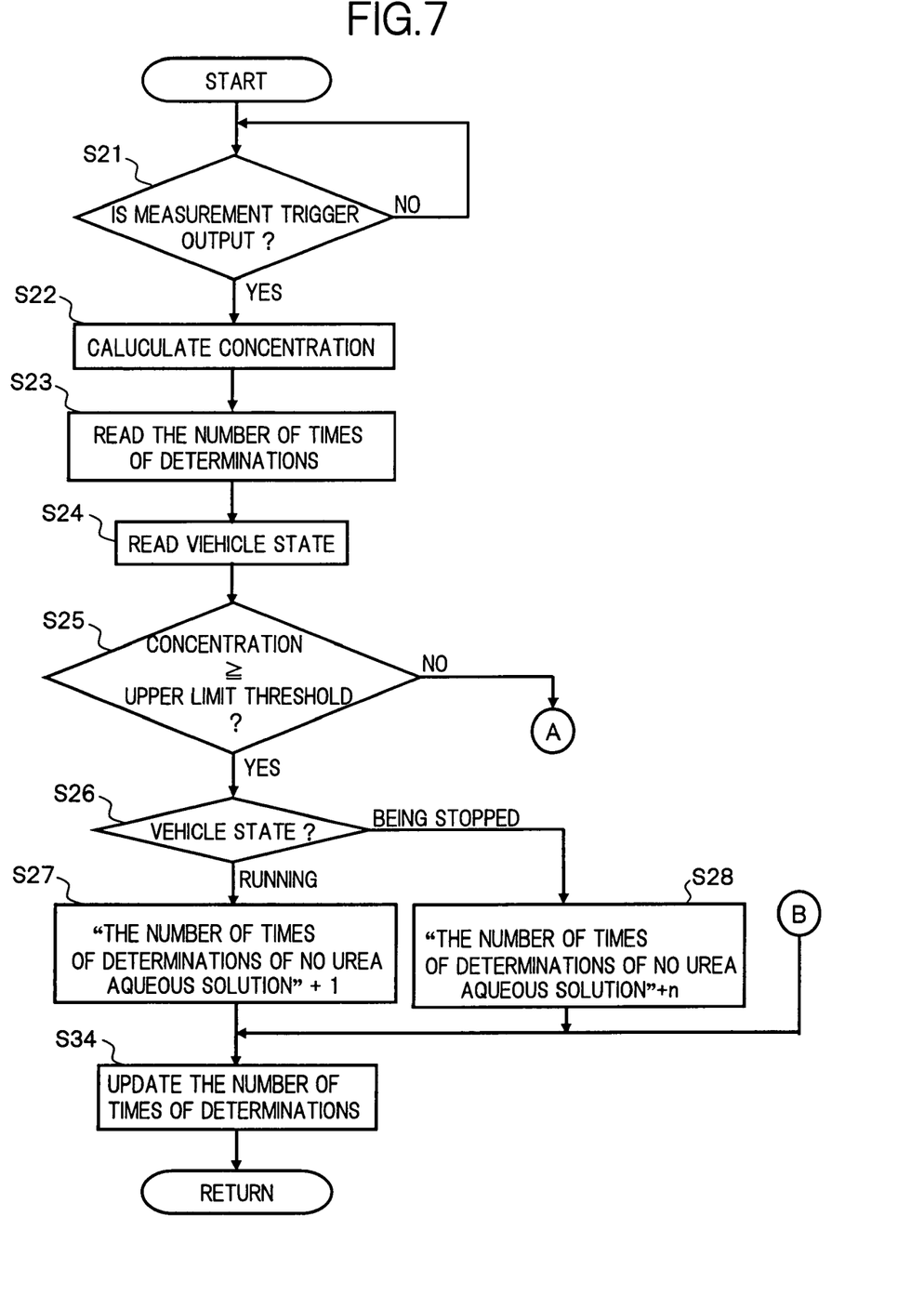
FIG. 7 is a flowchart showing a concentration calculating process and a counting process.
Figure 8:
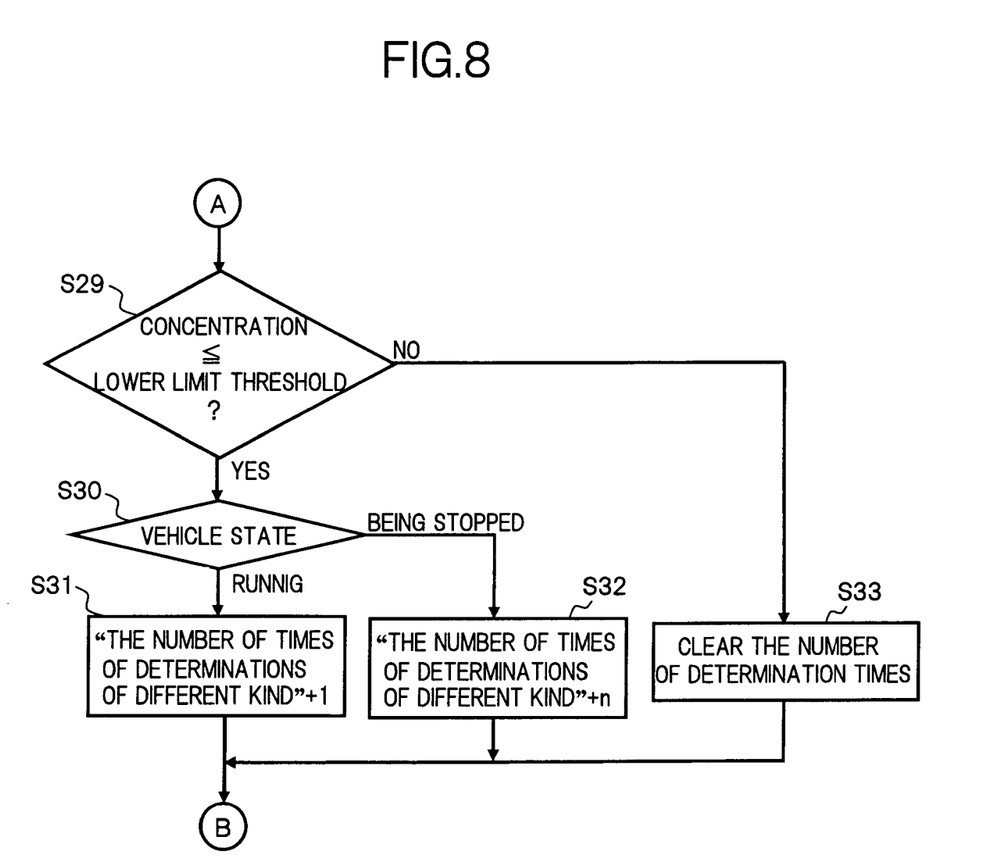
FIG. 8 is a flowchart showing the concentration calculating process and the counting process.

In FIGS. 7 and 8 showing the concentration calculating process and the counting process performed by the concentration calculating unit 34C and the counting unit 34D, in step 21, whether the measurement trigger is outputted or not is determined. When the measurement trigger is outputted (Yes), the program proceeds to step 22. When the measurement trigger is not outputted (No), the device waits.

In step 22, the concentration of the urea aqueous solution is calculated. That is, the heater A in the sensor 32 is operated only by the predetermined time $t_1$, and the concentration of the urea aqueous solution is calculated on the basis of the temperature rise characteristic in the temperature sensor B.

In step 23, the number of determination times stored in the memory is read. The number of determination times includes the number of times of determination of no urea aqueous solution, specifically, the number of times the concentration of the urea aqueous solution is successively determined to be equal to or higher than the predetermined upper limit threshold, and the number of times of determination of a different kind solution, specifically, the number of times the concentration of the urea aqueous solution is successively determined to be equal to or less than the predetermined lower limit threshold.

In step 24, data indicative of a vehicle state, that is, a state where the vehicle is being stopped or the vehicle is running is read from the memory.

In step 25, whether the urea aqueous solution concentration is equal to or higher than the upper limit threshold or not is determined. The upper limit threshold is a threshold for determining whether no urea aqueous solution remains or not. The upper limit threshold is set to the upper limit which cannot be usually detected even if convection occurs in the correct urea aqueous solution. When the urea aqueous solution concentration is equal to or higher than the upper limit threshold (Yes), the program proceeds to step 26. When the urea aqueous solution concentration is less than the upper limit threshold (No), the program proceeds to step 29.

In step 26, a branching process according to the vehicle state is performed. Specifically, when the vehicle is running (Yes), the program proceeds to step 27 where one is added to the number of times of determination of no urea aqueous solution. On the other hand, when the vehicle is being stopped (No), the program proceeds to step 28 where "n" (natural number of 2 or larger) is added to the number of times of determination of no urea aqueous solution.

In step 29 after it is determined in step 25 that the urea aqueous solution concentration is less than the upper limit threshold, whether the urea aqueous solution concentration is equal to or less than the lower limit threshold or not is determined. The lower limit threshold is a threshold for determining whether the urea aqueous solution is a solution of a different kind or not, and is set to a lower limit value which cannot be usually detected even if convection occurs in the correct urea aqueous solution. When the urea aqueous solution concentration is equal to or lower than the lower limit threshold (Yes), the program proceeds to step 30. When the urea aqueous solution concentration is higher than the lower limit threshold (No), the program proceeds to step 33, and each of the number of times of determination of no urea aqueous solution and the number of times of determination of a urea aqueous solution of a different type is cleared.

In step 30, the branching process according to the vehicle state is performed. When the vehicle is running (Yes), the program proceeds to step 31, and one is added to the number of times of determination of a urea aqueous solution of a different kind. On the other hand, when the vehicle state is a stopped state (No), the program proceeds to step 32 and "n" (natural number of 2 or larger) is added to the number of times of determination of a urea aqueous solution of a different kind.

In step 34, the number of times of determination stored in the memory is updated.

By the concentration calculating process and the counting process, each time the measurement trigger is outputted, the heater A of the sensor 32 is operated for the predetermined time $t_1$, and the urea aqueous solution concentration is calculated on the basis of the temperature rise characteristic in the temperature sensor B. When the urea aqueous solution concentration is equal to or higher than the upper limit threshold, one is added to the number of times of determination of no urea aqueous solution stored in the memory when the vehicle is running, and "n" is added when the vehicle is being stopped. On the other hand, when the urea aqueous solution concentration is equal to or less than the lower limit threshold, one is added to the number of times of determination of a urea aqueous solution of a different kind stored in the memory when the vehicle is running, and "n" is added when the vehicle is being stopped. When the urea aqueous solution concentration lies between the lower limit threshold and the upper limit threshold, it is determined that the possibility that the solution is the correct urea aqueous solution is high, and each of the number of times of determination of no urea aqueous solution and the number of times of determination of a urea aqueous solution of a different kind is cleared.

Figure 9:
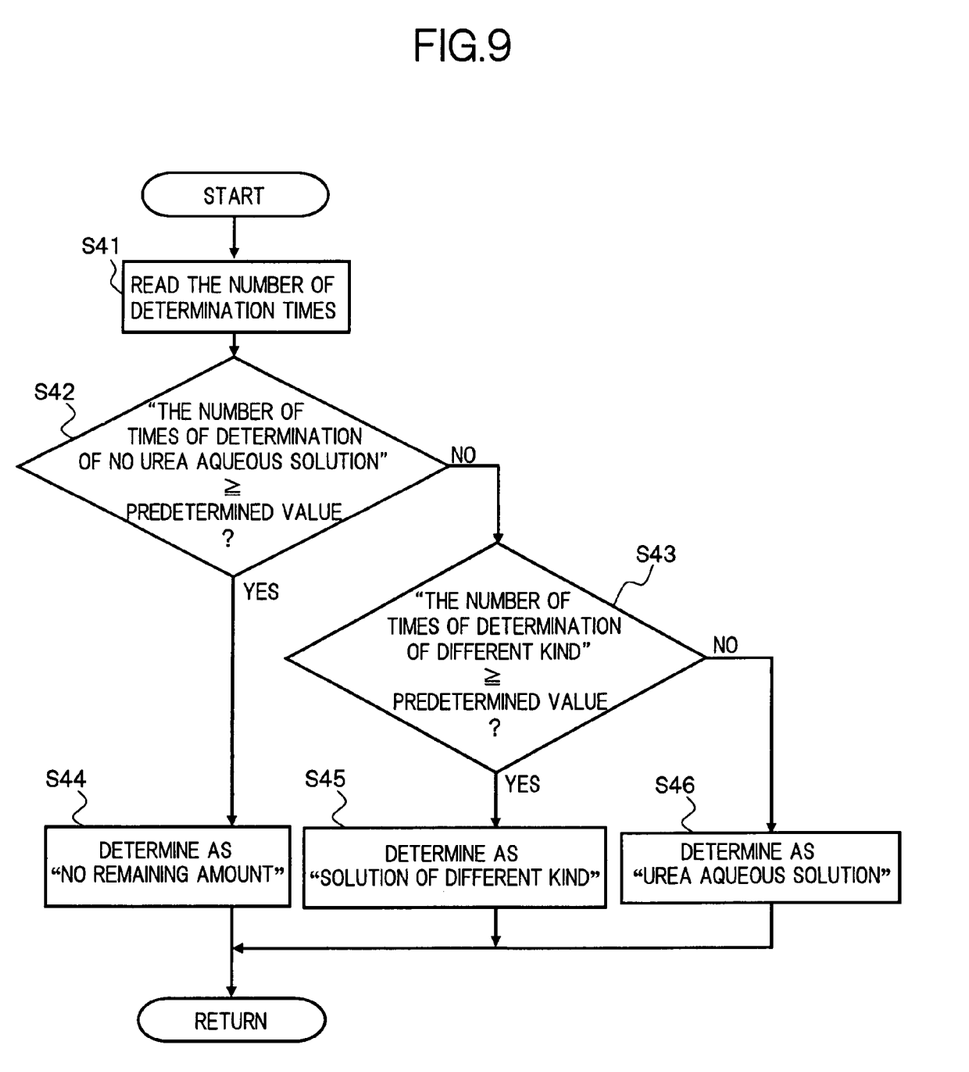
FIG. 9 is a flowchart showing a reducing agent determining process.

In FIG. 9 showing the reducing agent determining process properly executed by the reducing agent determining unit 34E, in step 41, the number of times of determination stored in the memory is read.

In step 42, whether the number of times of determination of no urea aqueous solution is equal to or larger than a predetermined value or not is determined. When the number of times of determination of no urea aqueous solution is equal to or larger than the predetermined value (Yes), the program proceeds to step 44 and it is determined that no urea aqueous solution remains. On the other hand, when the number of times of determination of no urea aqueous solution is less than the predetermined value (No), the program proceeds to step 43.

In step 43, whether the number of times of determination of a different kind is equal to or larger than the predetermined value or not is determined. When the number of times of determination of a different kind is equal to or larger than the predetermined number (Yes), the program proceeds to step 45 and it is determined that the urea aqueous solution is a solution of a different kind. On the other hand, when the number of times of determination of a different kind is less than the predetermined value (No), the program proceeds to step 46, and it is determined that the urea aqueous solution is correct one.

In the reducing agent determining process, when the number of times the concentration of the urea aqueous solution is successively determined to be equal to or higher than the upper limit threshold or to be equal to or lower than the lower limit threshold becomes a predetermined value or larger, it is determined that no urea aqueous solution remains or the urea aqueous solution is a solution of a different kind. On the other hand, when the urea aqueous solution concentration lies between the lower limit threshold and the upper limit threshold, it is determined that the urea aqueous solution is correct one.

Figure 10:
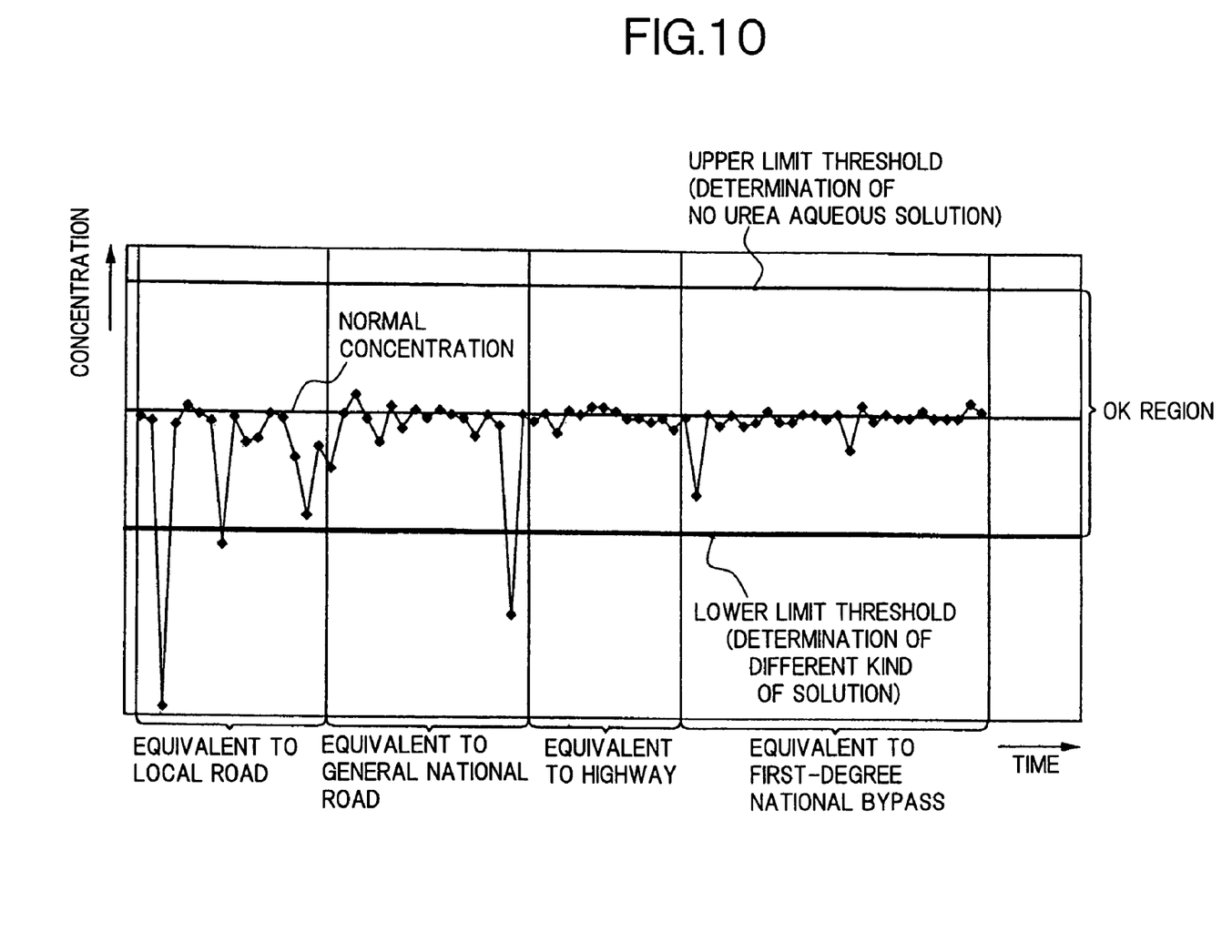
FIG. 10 is a sensor output characteristic diagram showing concentration measurement values during travel of a vehicle.

Specifically, when convection occurs in the urea aqueous solution, heat generated by the heater A in the sensor 32 is carried by the convection. Therefore, the amount of heat transmitted to the temperature sensor B decreases and the concentration detection accuracy deteriorates. However, when the output characteristics of the sensor 32 were actually measured, as shown in FIG. 10, it could be found out as follows. Namely, when the urea aqueous solution is correct, even if convection is generated, it can be understood as a true fact that occurrence of deviation of the sensor output from the predetermined range many times in a successive manner is quite rare.

By utilizing the true fact, when the number of times the concentration of the urea aqueous solution is successively determined to be equal to or higher than the upper limit threshold or is successively determined to be equal to or lower than the lower limit threshold becomes equal to or larger than a predetermined value, it is determined that no urea aqueous solution remains or the urea aqueous solution is a solution of a different kind. In such a manner, irrespective of the vehicle state, the state where the urea aqueous solution does not remain or is a solution of a different kind can be always determined. Since convection occurring in the urea aqueous solution is weak or no convection is generated when the vehicle is being stopped, by adding the value "n" larger than the value in the travel state to the number of determination times, the discrimination can be made in a short time.

To improve the discrimination accuracy, it is desirable to surround the detecting unit 32B of the sensor 32 by a box-like encasing member having an almost rectangular parallelepiped shape. With such a configuration, the urea aqueous solution around the detecting unit 32B is limited, and its convection is suppressed. Consequently, even when the vehicle is running, variations in the urea aqueous solution concentration detected by the sensor 32 are reduced, and it can be discriminated with high accuracy that the urea aqueous solution does not remain, the urea aqueous solution is a solution of a different kind, or the urea aqueous solution is correct one.

In the counting process shown in FIGS. 7 and 8, to simplify the control program, irrespective of the vehicle state, one (1) may be uniformly added to the number of times of determination of no urea aqueous solution when the urea aqueous solution concentration becomes equal to or higher than the upper limit threshold, and one may be uniformly added to the number of times of determination of a solution of different kind when the urea aqueous solution concentration becomes equal to or lower than the lower limit threshold.

In the reducing agent determining process shown in FIG. 9, when it is determined that the urea aqueous solution does not remain or is a solution of a different kind, the driver of the vehicle may be notified of the fact with an alarm or the like. In this case, the driver of the vehicle can grasp that the urea aqueous solution is not correct at an early stage and take a proper action such as replacement, thereby enabling the functions of the exhaust gas purifying apparatus to be maintained.

Further, it is also possible to write the number of times of determinations in the memory into an EEPROM (Electrically Erasable Programmable Read Only Memory) or the like as a nonvolatile memory when the engine 10 is stopped. It is also possible to read the number of times of determinations written in the EEPROM or the like to the memory when the engine 10 is started. In such a manner, the number of times of determinations before the engine 10 starts is taken over. It is unnecessary to count the number of times of determinations from the beginning each time the engine 10 is started, and discrimination of the urea aqueous solution can be performed in a short time.

Therefore, the liquid reducing agent discriminating apparatus according to the present invention can always discriminate one of such three conditions that there is no remainder of liquid reducing agent, there remains a solution of a different kind, and there remains correct liquid reducing agent even when the sensor for outputting a signal in relation to concentration of the liquid reducing agent on the basis of the characteristic of heat transmission between two points apart from each other within the storage tank is mounted on a mobile vehicle.

It should be appreciated that the entire contents of Japanese Patent Application No. 2004-315615, filed on Oct. 29, 2004, on which the convention priority is claimed is incorporated herein by reference.

It should also be understood that many modifications and variations of the described embodiments of the invention will occur to a person having an ordinary skill in the art without departing from the spirit and scope of the present invention as claimed in the appended claims.

We claim:
1. A liquid reducing agent discriminating apparatus comprising:
   a sensor disposed in a storage tank capable of storing a liquid reducing agent and configured to output a signal in relation to concentration of the liquid reducing agent on the basis of a characteristic of heat transmission between two points apart from each other within the storage tank; and a control unit having therein a computer, wherein the control unit:

outputs a measurement trigger at a predetermined time interval after start of an engine;

calculates concentration of the liquid reducing agent on the basis of the signal from the sensor when the measurement trigger is outputted;

counts each of first number of times that the concentration successively becomes equal to or higher than a predetermined upper limit threshold and second number of times that the concentration successively becomes equal to or lower than a predetermined lower limit threshold;

determines that there is no remainder of liquid reducing agent when the first number of times becomes equal to or larger than a predetermined value; and determines that there remains an incorrect solution other than the liquid reducing agent when the second number of times becomes equal to or larger than the predetermined value.

2. The liquid reducing agent discriminating apparatus according to claim 1, wherein a box-like encasing member having an almost rectangular parallelepiped shape is disposed to thereby surround a detecting unit of the sensor.

3. The liquid reducing agent discriminating apparatus according to claim 1, wherein when the engine is being stopped, the control unit writes the first number of times and the second number of times in a nonvolatile memory and, when the engine starts, the control unit reads the first number of times and the second number of times from the memory.

4. The liquid reducing agent discriminating apparatus according to claim 1, wherein when it is determined that there is no remainder of liquid reducing agent or there remains the incorrect solution other than the liquid reducing agent, the control unit notifies that there is no remainder of the liquid reducing agent or there remains the incorrect solution other than the liquid reducing agent.

5. The liquid reducing agent discriminating apparatus according to claim 1, wherein the control unit further determines whether the vehicle is running or stopped, and when it is determined that the vehicle is stopped, adds natural number of 2 or larger to the first or second number of times.

6. The liquid reducing agent discriminating apparatus according to claim 5, further comprising:

an engine rotating speed sensor configured to detect engine rotating speed; and a vehicle speed sensor configured to detect vehicle speed, wherein when the engine rotating speed detected by the engine rotating speed sensor is equal to or lower than a predetermined value and the vehicle speed detected by the vehicle speed sensor is equal to or lower than a predetermined value, the control unit determines that the vehicle is being stopped and, in the other cases, the control unit determines that the vehicle is running.

* * * * *